United States Patent [19]

Buzzetti et al.

[11] Patent Number: 4,824,830
[45] Date of Patent: Apr. 25, 1989

[54] 6- OR 7-METHYLENANDROSTA-1,4-DIENE-3,17-DIONE DERIVATIVES AND PROCESS FOR THEIR PREPARATION

[75] Inventors: Franco Buzzetti, Monza; Natale Barbugian, Milan; Paolo Lombardi, Milan; Enrico di Salle, Milan, all of Italy

[73] Assignee: Farmitalia Carlo Erba S.r.l., Milan, Italy

[21] Appl. No.: 70,685

[22] Filed: Jul. 7, 1987

[30] Foreign Application Priority Data

Jul. 14, 1986 [GB] United Kingdom ............... 8617107

[51] Int. Cl.$^4$ .......................... A61K 31/56; C07J 1/00
[52] U.S. Cl. .................................. 514/177; 260/397.3
[58] Field of Search ...................... 514/177; 260/397.3

[56] References Cited

U.S. PATENT DOCUMENTS 2,744,120  5/1956  Fried et al. ................... 260/343.2
4,235,893  11/1980  Brodie et al. ...................... 424/243
4,591,585  5/1986  Kerb et al. .......................... 514/177

FOREIGN PATENT DOCUMENTS 929985  6/1983  United Kingdom .

OTHER PUBLICATIONS

Chemical Abstracts, vol. 106 (1987) #162,586e; Di Salle et al.
Schering AG, "New 1-Alkyl-Androsta-1,-4-Diene-3,17-Dione..." Farmodoc; Pharmaceuticals, p. 9.
Brodie, A. "Overview of Recent Developments of Aromatase Inhibitors" Cancer Research (Suppl) 42,3312s-3314 Aug. 1982.
Covey et al., "A New Hypothesis Based on Suicide Substrate..." Cancer Research (Suppl) 42,3327s-333s, Aug. 1982.
Farmdoc Abstract U.S. 4289-762 Rich 27 06 80.
Farmdoc Abstract U.S. Patent 4322-416.
Metcalf et al, "Substrate-Induced Inactivation of Aromatase..."J. Am. Chem. Soc. 1981 103,3221-3222.
Derwent Publications Ltd. EP 100 566A.
Farmdoc Abstract GB 2100-601.
Chemical Abstracts U.S. 3,117,966 (Petrow) vol. 60 9336.
Chemical Abstracts U.S. 3,112,305, vol. 60, 9337.
Farmdoc Abstract, SA 65/4327.
Farmdoc Abstract, U.S. 3,356,694.
"Aromatase Inhibitors, Synthesis and Biological Activity of Androstenedione Derivatives", David A. Marsh et al., J. Med. Chem., 1985, pp. 788-795.
Chemical Abstracts, vol. 100, 1984; 100:96848q "Prostatic Cancer ...".

Primary Examiner—Leonard Schenkman
Assistant Examiner—Joseph A. Lipovsky
Attorney, Agent, or Firm—Armstrong, Nikaido, Marmelstein & Kubovcik

[57] ABSTRACT

The invention relates to new 6- or 7-methylenandrosta-1,4-diene-3,17-diones of the following formula

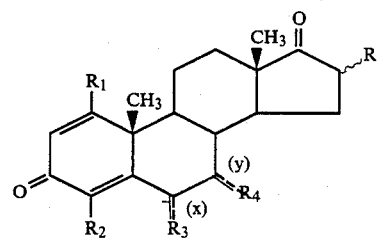

wherein R is hydrogen or fluorine; $R_1$ is hydrogen or $C_1$-$C_6$ alkyl; $R_2$ is hydrogen or halogen; one of $R_3$ and $R_4$ is =$CH_2$ and the other is hydrogen or $C_1$-$C_4$ alkyl, and when $R_3$ is =$CH_2$, at least one of R and $R_4$ is other than hydrogen; and the symbol (x)

represents a double bond and the symbol (y)

represents a single bond when $R_3$ is =$CH_2$ or the symbol (x)

represents a single bond and the symbol (y)

represents a double bond when $R_4$ is =$CH_2$, which are useful in therapy, in particular as anti-cancer agents.

8 Claims, No Drawings

6- OR 7-METHYLENANDROSTA-1,4-DIENE-3,17-DIONE DERIVATIVES AND PROCESS FOR THEIR PREPARATION

The present invention relates to new 6- or 7-methylenandrosta-1,4-diene-3,17-diones, to a process for their preparation, to pharmaceutical compositions containing them, and to the use of said compounds for the treatment of hormone-dependent cancers in mammals.

Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas.

Estrogens are also involves in the pathogenesis of benign prostatic hyperplasia.

Endogenous estrogens are ultimately formed from their androstenedione or testosterone as immediate precursors.

The reaction of central importance is the aromatization of the steroidic ring A, which is performed by the enzyme aromatase.

As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours.

Known steroidal substances which have been reported to be endowed with an aromatase-inhibiting action are, for example $\Delta^1$-testololactone [U.S. Pat. No. 2,744,120], 4-hydroxy-androst-4-ene-3,17-dione and esters thereof [see, for example, U.S. Pat. No. 4,325,893], 10-(1,2-propadienyl)-estr-4-ene-3,17-dione [U.S. Pat. No. 4,289,762], 10-(2-propynyl)-estr-4-ene-3,17-dione [J. Amer. Chem. Soc., 103, 3221 (1981) and U.S. Pat. No. 4,322,416], 19-thioandrostene derivatives (Europ. Pat. Appl. 100566), androsta-4,6-diene-3,17-dione, androsta-1,4,6-triene-3,17-dione [G.B. Pat Appl. No. 2,100,601A] and androsta-1,4-diene-3,17-dione [Cancer Res. (Suppl.) 42, 3327 (1982)].

The present invention provides compounds having the following general formula (1)

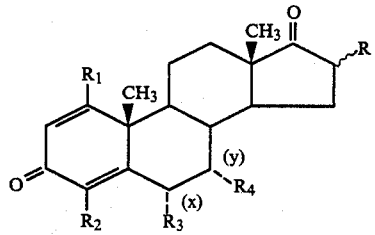

wherein
R is hydrogen or fluorine;
$R_1$ is hydrogen or $C_1$-$C_6$ alkyl;
$R_2$ is hydrogen or halogen;
one of $R_3$ and $R_4$ is =$CH_2$ and the other is hydrogen or $C_1$-$C_4$ alkyl, and when $R_3$ is =$CH_2$, at least one of R and $R_4$ is other than hydrogen, and the symbol $$\underline{(x)}$$

represents a double bond and the symbol $$\underline{(y)}$$

represents a single bond when $R_3$ is =$CH_2$ or the symbol $$\underline{(x)}$$

represents a single bond and the symbol $$\underline{(y)}$$

represents a double bond when $R_4$ is =$CH_2$.

The invention also includes within its scope all the possible isomers stereoisomers and their mixtures, and the metabolites and the metabolic precursors or bio-precursors of the compounds of formula (I).

In the formulae of the specification the heavy solid lines (━) indicate that a substituent is in the β-configuration, i.e. above the plane of the ring; a wavy line (∼) indicates that a substituent may be either in the α-configuration, i.e. below the plane of the ring, or in the β-configuration or in both, i.e. a mixture thereof. In particular when in the compounds of formula (I) $R_3$ is =$CH_2$, the $R_4$ substituent may be either in the α- or in the β-configuration or in both, i.e. a mixture thereof, and, respectively, when $R_4$ is =$CH_2$, then the $R_3$ substituent may be either in the α- or in β-configuration or in both, i.e. a mixture thereof.

Analogously the R substituent may be either in the α-configuration or β-configuration or in both, i.e. a mixture thereof.

Therefore the invention as stated above includes all the possible isomers, e.g. the single 16α,6α-; 16α,7α-; 16α,6β-; 16α,7β-; 16β,6α-; 16β,7α-; 16β,6β- and 16β,7β-epimers, as well as all the possible mixtures thereof, e.g. the 16(α,β),6α-; 16(α,β),6β-; 16(α,β),-6(α,β)-; 16(α,β),7α-; 16(α,β),7-β-; 16(α,β),7(α,β)-; 16α,6(α,β)-; 16α,7(α,β)-; 16β,6(α,β)-; 16β,7(α,β)-isomer. Hence for a compound of the invention, when occurring in a list of examples of specific compounds of the invention herein with no indication of its stereochemistry, the configuration of the 16- and/or 6- or 7-substituent, is intended to represent all the possible single epimers or mixtures thereof, as hereabove exemplified.

A halogen atom is e.g. fluorine, chlorine or bromine, in particular fluorine or chlorine, more preferably fluorine. A $C_1$-$C_4$ alkyl group is preferably a methyl or ethyl group, more preferably a methyl group. The alkyl radical may be a branched or straight chain group.

As stated above the present invention also includes whithin its scope pharmaceutically acceptable bio-precursors (otherwise known as pro-drugs) of the compounds of formula (I), i.e. compounds which have a different formula of formula (I) above but which nevertheless upon administration to a human being are converted directly or indirectly in vivo into a compound of formula (I).

Preferred compounds of the invention are the compounds of formula (I) wherein
R is hydrogen or fluorine
$R_1$ is hydrogen, methyl or ethyl
$R_2$ is hydrogen, chlorine or fluorine
one of $R_3$ and $R_4$ is $=CH_2$ and the other is methyl or ethyl.

Examples of specific compounds of the invention are the following compounds which, when appropriate, may be either α- or β-epimers or α,β mixtures of the said epimers:
16-fluoro-6-methylenandrosta-1,4-diene-3,17-dione;
16-fluoro-1-methyl-6-methylenandrosta-1,4-diene-3,17-dione;
16-fluoro-4-chloro-6-methylenandrosta-1,4-diene-3,17-dione;
4,16-difluoro-6-methylenandrosta-1,4-diene-3,17-dione;
16-fluoro-7-methyl-6-methyleneandrosta-1,4-diene-3,17-dione;
16-fluoro-1-methyl-4-chloro-6-methylenandrosta-1,4-diene-3,17-dione;
4,16-difluoro-1-methyl-6-methylenandrosta-1,4-diene-3,17-dione;
16-fluoro-1,7-dimethyl-6-methylenandrosta-1,4-diene-3,17-dione;
16-fluoro-4-chloro-7-methyl-6-methylenandrosta-1,4-diene-3,17-dione;
4,16-difluoro-7-methyl-6-methylenandrosta-1,4-diene-3,17-dione;
16-fluoro-1,7-dimethyl-4-chloro-6-methylenandrosta-1,4-diene-3,17-dione;
4,16-difluoro-1,7-dimethyl-6-methylenandrosta-1,4-diene-3,17-dione;
1,7-dimethyl-6-methylenandrosta-1,4-diene-3,17-dione;
7-methyl-6-methylenandrosta-1,4-diene-3,17-dione;
4-chloro-7-methyl-6-methylenandrosta-1,4-diene-3,17-dione;
4-fluoro-7-methyl-6-methylenandrosta-1,4-diene-3,17-dione;
7-methylenandrosta-1,4-diene-3,17-dione;
16-fluoro-7-methylenandrosta-1,4-diene-3,17-dione;
1-methyl-7-methylenandrosta-1,4-diene-3,17-dione;
4-chloro-7-methylenandrosta-1,4-diene-3,17-dione;
4-fluoro-7-methylenandrosta-1,4-diene-3,17-dione;
6-methyl-7-methylenandrosta-1,4-diene-3,17-dione;
16-fluoro-1-methyl-7-methylenandrosta-1,4-diene-3,17-dione;
16-fluoro-4-chloro-7-methylenandrosta-1,4-diene-3,17-dione;
16-fluoro-6-methyl-7-methylenanadrosta-1,4-diene-3,17-dione;
1-methyl-4-chloro-7-methylenandrosta-1,4-diene-3,17-dione;
1-methyl-4-fluoro-7-methylenandrosta-1,4-diene-3,17-dione;
1,6-dimethyl-7-methyleneandrosta-1,4-diene-3,17-dione;
4-chloro-6-methyl-7-methylenandrosta-1,4-diene-3,17-dione;
4-fluoro-6-methyl-7-methylenandrosta-1,4-diene-3,17-dione;
16-fluoro-1,6-dimethyl-4-chloro-7-methylenandrosta-1,4-diene-3,17-dione and
4,16-difluoro-1,6-dimethyl-7-methylenandrosta-1,4-diene-3,17-dione.

The compounds of the invention can be obtained by a process comprising:
(a) reacting a compound of formula (II)

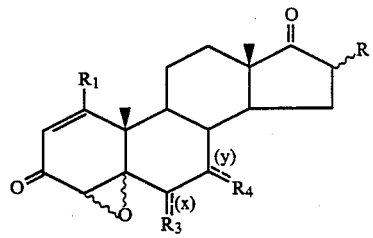

wherein, the symbols (x) and (y),

R, $R_1$, $R_3$ and $R_4$ are as defined above, with a hydrohalic acid, so obtaining a compound of formula (I), wherein $R_2$ is halogen and R, $R_1$, $R_3$ and $R_4$ are as defined above; or
(b) dehydrogenating a compound of formula (III)

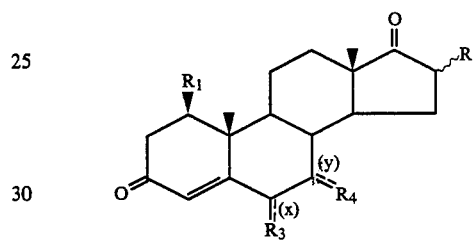

wherein, the symbols (x) and (y),

R, $R_1$, $R_3$ and $R_4$ are as defined above, so obtaining a compound of formula (I) wherein $R_2$ is hydrogen and R, $R_1$, $R_3$ and $R_4$ are as defined above; and, if desired, converting a compound of formula (I) into another compound of formula (I), and/or, if desired, separating a mixture of isomers of compounds of formula (I) into the single isomers.

The reaction of compound of formula (II) with a hydrohalic acid may be carried out according to known methods, e.g. B. Camerino et al. 1956; Il Farmaco II, 586. When the hydrohalic acid is the hydrochloric or hydrobromic one, such reaction is preferably performed in acetic acid or ethanol, at a temperature ranging from about 0° C. to about 100° C.

The dehydrogenation of compound of formula (III) may be carried out by treatment with a suitable dehydrogenating agent, e.g. dichlorodicyanobenzoquinone (DDQ), selenium dioxide, chloranil or benzeneseleninic anhydride. Preferably such reaction is performed by treatment with DDQ, in an inert solvent, such as dioxane, benzene, toluene or dichloromethane, at a temperature ranging from about 40° C. to about 100° C. and reaction times varying from about 12 to 72 hours.

The separation of a mixture of isomers into the single isomers as well as the conversion of a compound of formula (I) into another compound of formula (I) may be carried out according to known methods. For example a 6β-methyl derivative of a compound of formula (I) may be converted into the respective 6α-methyl derivative by heating to reflux in a lower alkyl aliphatic alcohol, e.g. ethanol, with a basic agent, e.g. 0.1N sodium hydroxide.

The conversion of a β-methyl derivative into the respective α-methyl derivative may be performed, if desired, also on the intermediate compounds herein described, e.g. those of formula (III), by following the same procedure.

The compounds of formula (II) may be prepared by dehydrogenation of a compound of formula (IV)

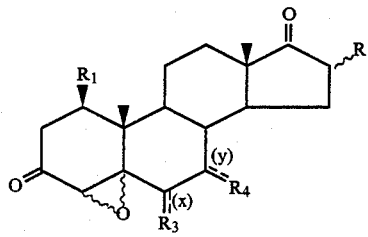
(IV)

wherein, the symbols (x) and (y),

R, R$_1$, R$_3$ and R$_4$ are as defined above.

The dehydrogenation of a compound of formula (IV) may be performed according to known methods, e.g. by treatment with DDQ, according to D. Walker and J. D. Heibert: Chem. Rev. 67, 156 (1967), or by treatment with selenium dioxide, chloranil or benzeneseleninic anhydride. Preferably the reaction is performed by treatment with benzeneseleninic anhydride in an inert organic solvent, such as chlorobenzene or carbon tetrachloride, at a temperature ranging from about 60° C. to about 120° C. and reaction times varying from about 2 hours to about 48 hours.

The compounds of formula (III), wherein R$_3$ represents =CH$_2$ and R, R$_1$ and R$_4$ are as defined above, may be obtained by methylenation of a compound of formula (V)

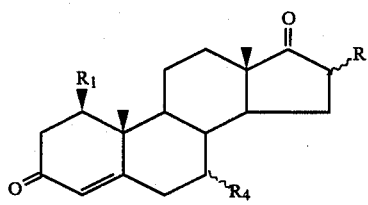
(V)

wherein
R, R$_1$ and R$_4$ are as defined above.

Methylenation, i.e. 6-methylenation, of a compound of formula (V) may be carried out according to known methods, e.g. according to K. Annen et al. Synthesis 1982, 34. Preferably a compound of formula (V) is reacted with formaldehyde diethylacetal in a suitable organic solvent, e.g. chloroform, at reflux temperature, in the presence of a condensing agent, e.g. phosphoryl chloride and sodium acetate. Alternatively, the same reaction may be carried out in other inert organic solvents, e.g. 1,2-dichloroethane, diethylether or dioxane and in the presence of other suitable condensing agents, e.g. phosphorous pentoxide or p-toluenesulfonic acid.

The compounds of formula (III), wherein R$_4$ represents =CH$_2$, R$_3$ is hydrogen and R and R$_1$ are as defined above, may be obtained by reduction of a compound of formula (VI)

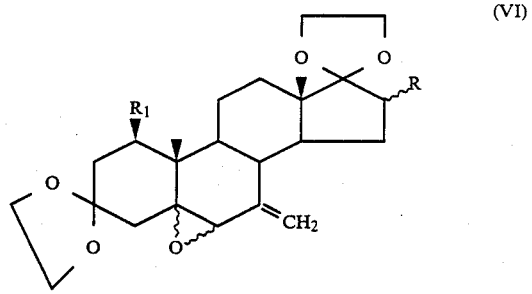
(VI)

wherein R and R$_1$ are as defined above, followed by hydrolysis and dehydration. Reduction of a compound of formula (VI) may be carried out according to known methods, e.g. as described in "Complex Hydrides" by Andor Hajos (Elsevier Ed. 1979). Preferably the reduction is performed in a lower alkyl ether (e.g. diethyl ether) solution, with lithium aluminium hydride at temperatures ranging from about 0° C. to the reflux temperature.

The subsequent hydrolysis of the ketal groups may be performed e.g. in acidic conditions at a temperature ranging from about 0° C. to boiling temperature. Preferably the acidic hydrolysis is carried out by treatment with a 2:1 mixture of glacial acetic acid and water, at a temperature ranging from about 20° C. to about 60° C. The final dehydration generally occurs during the hydrolysis step. Alternatively it may be performed in pyridine solution with thionyl chloride at temperatures ranging from about 0° C. to about 30° C.

The compounds of formula (III) wherein R$_4$ represents =CH$_2$, R$_3$ is C$_1$-C$_4$ alkyl and R and R$_1$ are as defined above, may be obtained by Grignard reaction on a compound of formula (VI), as defined above, followed by hydrolysis and dehydration. The Grignard reaction on a compound of formula (VI) may be carried out according to reaction conditions well known in organic chemistry, e.g. as described in "Grignard reactions of nonmetallic substances" by M. S. Kharasch and O. Reinmuth. Preferably the Grignard reagent is prepared in diethyl ether solution by reaction of a suitable C$_1$-C$_4$ alkyl iodide with magnesium.

Then a compound of formula (VI), dissolved in suitable solvent e.g. benzene or tetrahydrofuran, is added and the mixture heated to reflux. Alternatively the Grignard reagent may be prepared from a suitable C$_1$-C$_4$ alkyl bromide or chloride and using a suitable di(C$_1$-C$_4$ alkyl)ether. The subsequent hydrolysis and dehydration steps may be carried out according to known methods, e.g. as described above.

The compounds of formula (IV) may be obtained by epoxidation of a compound of formula (III), as defined above. Epoxidation of a compound of formula (III) may be performed by treatment with a suitable oxidizing agent, preferably concentrated, e.g. 36%, hydrogen peroxide, in alcoholic alkali metal hydroxide solution, preferably KOH or NaOH in methanol, at a temperature ranging from about 0° C. to about 30° C., for reaction times varying from about 2 hours to about several days.

The compounds of formula (V) wherein R$_1$ is as defined above and R and R$_4$ are hydrogen are known compounds or may be obtained by known methods from known compounds. Analogously the compounds of formula (V), wherein R and R$_4$ have the meanings stated above, may be obtained starting from a compound of formula (V), wherein R and $R_4$ are hydrogen, through methods known in organic chemistry.

The compounds of formula (VI) may be obtained by methylenation of a compound of formula (VII)

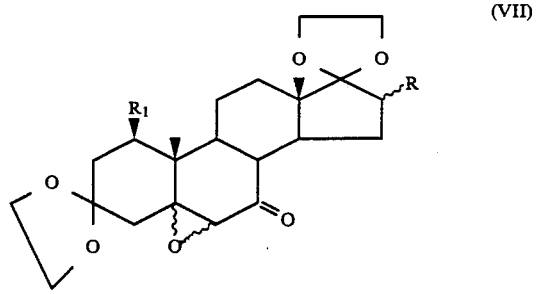

(VII)

wherein R and $R_1$ are as defined above.

The methylenation of a compound of formula (VII) may be performed e.g. by Wittig reaction according to known procedures. The compounds of formula (VII) may be obtained by following known procedures and starting from known compounds, for example they may be obtained starting from a compound of formula (V) as defined above, wherein R and $R_4$ are both hydrogen.

When in the new compounds of the present invention and in the intermediate products thereof groups are present, which need to be protected before submitting them to the hereabove illustrated reactions, they may be protected before the reactions take place and then deprotected at the end of the reaction, according to well known methods in organic chemistry.

The compounds of the present invention are inhibitors of the biotransformation of androgens into estrogens, i.e., they are steroidal aromatase inhibitors.

The aromatase inhibitory activity of these compounds was demonstrated by employing the in vitro test described by Thompson and Siiteri (E. A. Thompson and P. K. Siiteri, J. Biol. Chem. 249, 5364, 1974) which utilizes the human placental microsomal fraction as enzyme source. In this test the aromatization rate of androstenedione into estrone was evaluated by incubating [$1\beta,2\beta$-$^3$H]androstenedione (50 nM) in the presence of NADPH with the enzyme preparation and by measuring the amount of $^3H_2O$ formed during 20 min incubation at 37° C.

The new compounds, incubated at various concentrations, showed a relevant aromatase inhibitory activity.

By virtue of their ability to inhibit aromatase and, consequently, to reduce estrogen levels, the new compounds are useful in the treatment and prevention of various estrogen dependent diseases, i.e., breast, endometrial, ovarian and pancreatic cancers, gynecomastia, benign breast disease, endometriosis, polycystic ovarian disease and precocious puberty. Another application of the compounds of the invention is in the therapeutic and/or prophylactic treatment of prostatic hyperplasia, a disease of the estrogen dependent stromal tissue. The new compounds can find also use for the treatment of male infertility associated with oligospermia and for female fertility control, by virtue of their ability to inhibit ovulation and egg nidation.

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment we found to be negligible.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 150–200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention.

EXAMPLE 1

A mixture of sodium acetate (1 g), absolute chloroform (30 ml), formaldehyde diethyl acetal (30 ml, 0.24 mol), phosphoryl chloride (3.8 ml, 0.04 mol), and 1β,7α-dimethyl-16α-fluoroandrost-4-ene-3,17-dione (0.896 g, 2.7 mmol) is stirred at reflux for about 5 hrs, i.e. until the starting material has disappeared. The suspension is allowed to cool and under vigorous stirring a saturated sodium carbonate solution is added dropwise until the pH of the aqueous layer becomes alkaline. The organic layer is separated, washed to neutrality with water, and dried with sodium sulfate. After concentration under reduced pressure the oily residue is purified by chromatography on silica gel using hexane/ethyl acetate as eluant. Thus the pure 1β,7α-dimethyl-16α-fluoro-6-methylenandrost-4-ene-3,17-dione is obtained in 60% yield (0.56 g).

0.560 g of 1β,7α-dimethyl-16α-fluoro-6-methylenandrost-4-ene-3,17-dione and 0.59 g of dichlorodicyanobenzoquinone is refluxed in 20 ml of anhydrous dioxane for about 15 hrs. The the reaction mixture is filtered, the solvent removed in vacuo, the residue dissolved in ethyl acetate, the organic layer washed with water, dried over sodium sulfate and the solvent evaporated under vacuum. The crude product is chromatographed on silica gel using hexane/ethyl acetate 40% as eluant to yield 0.42 g of pure 1,7α-dimethyl-16α-fluoro-6-methylenandrosta-1,4-diene-3,17-dione.

Found: C 77.05, H 7.80, F 5.45. $C_{22}H_{27}FO_2$ requires: C 77.16, H 7.95, F 5.55.

According to the above described procedure and starting from the appropriate compound of formula (V) one can prepare also the 7α,16β-, the 7β,16α- and the 7β,16β-epimers of the above end-product, as well as their α,β-mixtures and furthermore the following compounds both as single α- or β-isomers and as a mixture thereof:

16-fluoro-6-methylenandrosta-1,4-diene-3,17-dione;
16-fluoro-1-methyl-6methylenandrosta-1,4-diene-3,17-dione;
1,7-dimethyl-6-methylenandrosta-1,4-diene-3,17-dione;
7-methyl-6-methylenandrosta-1,4-diene-3,17-dione,
N.M.R.δp.p.m.: 0.91 (3H, d); 0.94 (3H, s); 1.16 (3H, s); 4.97 (2H, m); 6.14 (1H, d); 6.27 (1H, d); 7.08 (1H, d).
MS (m/Z): 310;
16-fluoro-7-methyl-6-methylenandrosta-1,4-diene-3,17-dione, and
7-butyl-6-methylenandrosta-1,4-diene-3,17-dione.

EXAMPLE 2

To a solution of potassium tert-butoxide (449 mg) in dimethyl sulfoxide (20 ml) methyl triphenyl phosphonium iodide (1616 mg) is added portionwise at 20°–25° C. under nitrogen and the mixture kept for another 30 min at this temperature.

Then a dimethyl sulfoxide solution (10 ml) of 3,17-bis(ethylenedioxy)-5,6α-epoxy-16α-fluoro-1β-methyl-androstan-7-one (433 mg) is added and the mixture heated gradually to 40° C. during a period of 4 hrs. The reaction mixture poured onto ice, the product extracted with ethyl acetate, the organic layer washed with water, dried and evaporated under vacuum. The residue is chromatographed on silica gel and eluted with hexane/ethylacetate to give pure 3,17-bis(ethylenedioxy)-5,6α-epoxy-16α-fluoro-1β-methyl-7-methylenandrostane (344 mg).

3,17-bis(ethylenedioxy)-5,6α-epoxy-16α-fluoro-1β-methyl-7-methylenandrostane (431 mg) in benzene solution (40 ml), is added to a Grignard mixture prepared from magnesium (122 mg) and methyl iodide (710 mg) in diethylether (10 ml). Solvent is removed until the boiling point reaches ~78° C. Heating is then continued for a further 3 hrs. Ice and saturated ammonium chloride solution are added, the product extracted with ethyl acetate and the organic layer is evaporated in vacuo after having washed and dried it. The residue is dissolved in a 2:1 mixture of acetic acid and water (10 ml) and the solution heated for about 6 hrs at 40°–50° C. Then water is added and the product extracted with ethyl acetate. The organic layer is washed with sodium bicarbonate solution, dried and evaporated in vacuo. The residue is submitted to column chromatography thus giving pure 16α-fluoro-1β,6β-dimethyl-7-methylenandrost-4-ene-3,17-dione (275 mg).

A ethanol solution (10 ml) of 16α-fluoro-1β,6β-dimethyl-7-methylenandrost-4-ene-3,17-dione (344 mg), which contains 0.1N sodium hydroxide (1 ml), is heated to reflux for about 30 min. Then the ethanol is removed in vacuo and the residue taken up in benzene. The organic phase is washed to neutrality with water, dried and evaporated. The residue is submitted to chromatographic purification as described above to give the isomeric 16α-fluoro-1β,6α-dimethyl-7-methylenandrost-4-ene-3,17-dione (292 mg).

A mixture of 16α-fluoro-1β,6α-dimethyl-7-methylenandrost-4-ene-3,17-dione (344 mg) and dichlorodicyanobenzoquinone (363 mg) in dioxane (20 ml) is refluxed for about 15 hours. Then the resulting suspension is cooled, the precipitate filtered off and the filtrate evaporated in vacuo. The residue is dissolved in ethyl acetate, the organic layer washed with water, dried over sodium sulfate and the solvent removed under vacuum. The crude product is chromatographed on silica gel using hexane/ethyl acetate as eluant to yield 16α-fluoro-1,6α-dimethyl-7-methylenandrosta-1,4-diene-3,17-dione (222 mg).

Found: C 77.08, H 7.89, F 5.51. $C_{22}H_{27}FO_2$ requires: C 77.16, H 7.95, F 5.55.

According to the above described procedure and starting from the appropriate compound of formula (VII) one can prepare the 16α,6β-, the 16β,6α- and the 16β,6β-epimers of the above compound, as well as their α,β-mixtures, and, furthermore, both the following compounds as single α- or β-isomers and as a mixture thereof:

6-methyl-7-methylenandrosta-1,4-dione-3,17-dione;
16-fluoro-6-methyl-7-methylenandrosta-1,4-diene-3,17-dione; and
1,6-dimethyl-7-methylenandrosta-1,4-diene-3,17-dione.

EXAMPLE 3

To a solution of lithium aluminium hydride (38 mg) in diethylether (10 ml) is added gradually a solution of 3,17-bis(ethylenedioxy)-5,6α-epoxy-16α-fluoro-1β-methyl-7-methylenandrostane (431 mg) in tetrahydrofuran (10 ml). The resulting mixture is stirred at 20°–25° C. for a period of about 18 hrs after which an aqueous solution of potassium sodium tartrate is added. The mixture is filtered and concentrated to a small volume under reduced pressure. The concentrate is taken up in diethyl ether and washed well with water. The ether solution is dried over magnesium sulfate, filtered and the ether removed under vacuum to yield crude 3,17-bis(ethylenedioxy)-16-fluoro-5-hydroxy-1β-methyl-7-methylenandrostane. This intermediate is dissolved in a 2:1 mixture of acetic acid and water (5 ml) and the solution heated for 6 hrs at 40°–50° C. Then water is added and the product extracted with ethyl acetate.

The organic layer is washed with sodium bicarbonate solution, dried and evaporated in vacuo. The residue is purified by column chromatography on silica gel thus giving pure 16α-fluoro-1β-methyl-7-methylenandrost-4-ene-3,17-dione (198 mg). 16α-fluoro-1β-methyl-7-methylenandrost-4-ene-3,17-dione (331 mg) and dichlorodicyanobenzoquinone (363 mg) are refluxed in dioxane solution (20 ml) for about 15 hrs. Then the precipitate is filtered off and the filtrate evaporated in vacuo. The residue is taken up in ethyl acetate and the organic solution washed, dried and evaporated in vacuo. The residue is chromatographed on silica gel using hexane/ethyl acetate as eluant to give pure 16α-fluoro-1-methyl-7-methylenandrosta-1,4-diene-3,17-dione (230 mg).

Found: C 76.75, H 7.55, F 5.70. $C_{21}H_{25}FO_2$ requires C 76.80, H 7.67, F 5.79.

By proceeding analogously and starting from the appropriate compound of formula (VI) one can prepare the above end-product as 16β-epimer and as 16(α,β)-mixture, the compound 16-fluoro-7-methylenandrosta-1,4-diene-3,17-dione, as 16α-epimer, 16β-epimer and 16(α,β)-epimeric mixture and, furthermore, the compounds 1-methyl-7-methylenandrosta-1,4-diene-3,17-dione and 7-methylenandrosta-1,4-diene-3,17-dione.

EXAMPLE 4

345 mg of 16α-fluoro-1β,6β-dimethyl-7-dimethylenandrost-4-ene-3,17-dione (its preparation is described in Example 2) is dissolved in methanol (20 ml) and the resulting solution cooled to 0° C. Thereupon ice cold 36% hydrogen peroxide (2 ml) and 2% sodium hydroxide (1 ml) are added. The mixture is stirred for about 24 hrs at 0°-5° C. and then poured into ice water. The product is filtered off, washed with water and then dried to give 4,5-epoxy-16α-fluoro-1β,6β-dimethyl-7-methylenandrostane-3,17-dione.

A solution of 4,5-epoxy-16α-fluoro-1β,6β-dimethyl-7-methylenandrostane-3,17-dione (361 mg) and benzeneseleninic anhydride (360 mg) in chlorobenzene (30 ml) is heated for 4 hrs at 90°-100° C. Then the solvent is removed in vacuo and the residue chromatographed on silica gel to give 4,5-epoxy-16α-fluoro-1,6β-dimethyl-7-methylenandrost-1-ene-3,17-dione (287 mg).

A solution of 4,5-epoxy-16α-fluoro-1,6β-dimethyl-7-methylenandrost-1-ene-3,17-dione (359 mg) in glacial acetic acid (5 ml) is treated with gaseous hydrogen chloride for about 30 min at room temperature. The precipitate is filtered off, washed with diethylether and then chromatographed on silica gel to give pure 4-chloro-16α-fluoro-1,6β-dimethyl-7-methylen-androsta-1,4-diene-3,17-dione (245 mg).

Found: C 70.05, H 6.85, C 19.39, F 4.95. $C_{22}H_{26}ClFO_2$ requires: C 70.11, H 6.95, Cl 9.41, F 5.04.

Following the above described procedure and starting from the appropriate compound of formula (111) one can prepare the 16β,6β-, the 16β,6α- and the 16α,-6α-epimers of the above end-product as well as their α,β mixtures, and, furthermore, the following compounds which, when appropriate, may be either single α- or β-isomers or mixtures thereof:
4-chloro-7-methylenandrosta-1,4-diene-3,17-dione;
4-fluoro-7-methylenanadrosta-1,4-diene-3,17-dione;
4-chloro-16-fluoro-7-methylenandrosta-1,4-diene-3,17-dione;
4,16-difluoro-7-methylenandrosta-1,4-diene-3,17-dione;
4-chloro-1-methyl-7-methylenandrosta-1,4-diene-3,17-dione;
4-fluoro-1-methyl-7-methylenandrosta-1,4-diene-3,17-dione;
4-chloro-6-methyl-7-methylenandrosta-1,4-diene-3,17-dione;
4-fluoro-6-methyl-7-methylenandrosta-1,4-diene-3,17-dione;
4-chloro-16-fluoro-1-methyl-7-methylenandrosta-1,4-diene-3,17-dione;
4,16-difluoro-1-methyl-7-methylenandrosta-1,4-diene-3,17-dione;
4-chloro-1,6-dimethyl-7-methylenandrosta-1,4-diene-3,17-dione;
4-fluoro-1,6-dimethyl-7-methylenandrosta-1,4-diene-3,17-dione;
4-chloro-16-fluoro-6-methyl-7-methylenandrosta-1,4-diene-3,17-dione;
4,16-difluoro-6-methyl-7-methylenandrosta-1,4-diene-3,17-dione; and
4,16-difluoro-1,6-dimethyl-7-methylenandrosta-1,4-diene-3,17-dione.

EXAMPLE 5

344 mg of 16α-fluoro-1β,7α-dimethyl-6-methylenandrost-4-ene-3,17-dione (which can be prepared as described in Example 1) are dissolved in methanol (20 ml) and the solution cooled to 0°-5° C. Ice cold 36% hydrogen peroxide (2 ml) and 2% sodium hydroxide (1 ml) are added and the mixture stirred for further 24 hrs at 0°-5° C. Then the mixture is poured into ice water, the product filtered off, washed with water and dried to yield 16α-fluoro-4,5-epoxy-1β,7α-dimethyl-6-methylenandrostane-3,17-dione (306 mg).

A solution of 16α-fluoro-4,5-epoxy-1β,7α-dimethyl-6-methylenandrost-4-ene-3,17-dione (361 mg) and benzeneseleninic anhydride (360 mg) in chlorobenzene (30 ml) is heated for 4 hrs at 90°-100° C. The solvent is evaporated in vacuo and the residue submitted to column chromatography on silica gel using hexane/ethyl acetate as eluant thus giving pure 16α-fluoro-4,5-epoxy-1,7α-dimethyl-6-methylen-androst-1-ene-3,17-dione (269 mg).

Gaseous hydrogen chloride is introduced for about 30 min into a solution of 16α-fluoro-4,5-epoxy-1,7α-dimethyl-6-methylenandrost-1-ene-3,17-dione (359 mg) in glacial acetic acid (5 ml). Thereupon water is added, the precipitate filtered off, washed with diethylether and chromatographed on silica gel to yield pure 16α-fluoro-4-chloro-1,7α-dimethyl-6-methylenandrosta-1,4-diene-3,17-dione (264 mg). Found: C 70.05, H 6.89, Cl 9.32, F 4.99. $C_{22}H_{26}ClFO_2$ requires: C 70.11, H 6.95, Cl 9.41, F 5.04.

Using the same procedure and starting from the appropriate compound of formula (III) one can prepare the 16α,7β-, the 16β,7α- and the 16β,7β-epimers of the above end-product as well as their α-β-mixtures, and, furthermore, the following compounds both as single α- or β-isomers and as mixtures thereof:
16-fluoro-4-chloro-6-methylenandrosta-1,4-diene-3,17-dione;
4,16-difluoro-6-methylenandrosta-1,4-diene-3,17-dione;
4-chloro-7-methyl-6-methylenandrosta-1,4-diene-3,17-dione;
4-fluoro-7-methyl-6-methylenandrosta-1,4-diene-3,17-dione;
16-fluoro-4-chloro-1-methyl-6-methylenandrosta-1,4-diene-3,17-dione;
4,16-difluoro-1-methyl-6-methylenandrosta-1,4-diene-3,17-dione;

4-chloro-1,7-dimethyl-6-methylenandrosta-1,4-diene-3,17-dione;

4-fluoro-1,7-dimethyl-6-methylenandrosta-1,4-diene-3,17-dione;

16-fluoro-4-chloro-7-methyl-6-methylenandrosta-1,4-diene-3,17-dione;

4,16-difluoro-7-methyl-6-methylenandrosta-1,4-diene-3,17-dione; and 4,16-difluoro-1,7-dimethyl-6-methylenandrosta-1,4-diene-3,17-dione.

EXAMPLE 6

Tablets each weighing 0.150 g and containing 25 mg of the active substance, can be manufactured as follows:

| Composition (for 10000 tablets) | |
|---|---|
| 7α-methyl-6-methylenandrosta-1,4-diene-3,17-dione | 250 g |
| Lactose | 800 g |
| Corn starch | 415 g |
| Talc powder | 30 g |
| Magnesium stearate | 5 g |

The 7α-methyl-6-methylenandrosta-1,4-diene-3,17-dione, the lactose and half the corn starch are mixed; the mixture is then forced throught a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 7

Capsules, each dosed at 0.200 g and containing 20 mg of the active substance can be prepared.

| Composition for 500 capsules: | |
|---|---|
| 7α-methyl-6-methylenandrosta-1,4-diene-3,17-dione | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (1)

wherein
R is hydrogen or fluorine;
$R_1$ is hydrogen or $C_1$–$C_6$ alkyl;
$R_2$ is hydrogen or halogen;
one of $R_3$ and $R_4$ is $=CH_2$ and the other is hydrogen or $C_1$–$C_4$ alkyl, and when $R_3$ is $=CH_2$, at least one of R and $R_4$ is other than hydrogen; and the symbol (x)

represents a double bond and the symbol (y)

represents a single bond when $R_3$ is $=CH_2$ or the symbol (x)

represents a single bond and the symbol (y)

represents a double bond when $R_4$ is $=CH_2$.

2. A compound of formula (1), according to claim 1, wherein
R is hydrogen or fluorine;
$R_1$ is hydrogen, methyl or ethyl;
$R_2$ is hydrogen; chlorine or fluorine; and one of $R_3$ and $R_4$ is $=CH_2$ and the other is methyl or ethyl.

3. A process for the preparation of a compound of formula (I), according to claim 1, said process comprising:

(a) reacting a compound of formula (II)

wherein the symbols (x) and (y),

R, $R_1$, $R_3$ and $R_4$ are as defined in claim 1, with a hydrohalic acid, so obtaining a compound of formula (I), wherein $R_2$ is halogen and R, $R_1$, $R_3$ and $R_4$ are as defined in claim 1; or (b) dehydrogenating a compound of formula (III)

wherein the symbols (x) and (y),

R, $R_1$, $R_3$ and $R_4$ are as defined in claim 1, so obtaining a compound of formula (I) wherein $R_2$ is hydrogen and R, $R_1$, $R_3$ and $R_4$ are as defined in claim 1; and, if desired, converting a compound of formula (I) into another compound of formula (I), and/or, if desired, separating a mixture of isomers of compounds of formula (I) into the single isomers.

4. A pharmaceutical composition containing a suitable carrier and/or diluent and, as an active principle, a therapeutically effective amount of a compound of formula (I) according to claim 1.

5. A method for the treatment of hormone-dependent breast, pancreatic, endometrial and ovarian cancers, in patients in need thereof, said method comprising administering to said patients an effective amount of a compound of claim 1.

6. A method for the treatment of prostatic hyperplasia in patients in need thereof, said method comprising administering to said patients an effective amount of a compound of claim 1.

7. A compound selected from the group consisting of:
16-fluoro-6-methylenandrosta-1,4-diene-3,17-dione;
16-fluoro-1-methyl-6-methylenandrosta-1,4-diene-3,17-dione;
16-fluoro-4-chloro-6-methylenandrosta-1,4-diene-3,17-dione;
4,16-difluoro-6-methylenandrosta-1,4-diene-3,17-dione;
16-fluoro-7-methyl-6-methylenandrosta-1,4-diene-3,17-dione;
16-fluoro-1-methyl-4-chloro-6-methylenandrosta-1,4-diene-3,17-dione;
4,16-difluoro-1-methyl-6-methylenandrosta-1,4-diene-3,17-dione;
16-fluoro-1,7-dimethyl-6-methylenandrosta-1,4-diene-3,17-dione;
16-fluoro-4-chloro-7-methyl-6-methylenandrosta-1,4-diene-3,17-dione;
4,16-difluoro-7-methyl-6-methylenandrosta-1,4-diene-3,17-dione;
16-fluoro-1,7-dimethyl-4-chloro-6-methylenandrosta-1,4-diene-3,17-dione;
4,16-difluoro-1,7-dimethyl-6-methylenandrosta-1,4-diene-3,17-dione;
1,7-dimethyl-6-methylenandrosta-1,4-diene-3,17-dione;
7-methyl-6-methylenandrosta-1,4-diene-3,17-dione;
4-chloro-7-methyl-6-methylenandrosta-1,4-diene-3,17-dione;
4-fluoro-7-methyl-6-methylenandrosta-1,4-diene-3,17-dione;
16-fluoro-7-methylenandrosta-1,4-diene-3,17-dione;
6-methyl-7-methylenandrosta-1,4-diene-3,17-dione;
16-fluoro-1-methyl-7-methylenandrosta-1,4-diene-3,17-dione;
16-fluoro-4-chloro-7-methylenandrosta-1,4-diene-3,17-dione;
16-fluoro-6-methyl-7-methylenanadrosta-1,4-diene-3,17-dione;
1,6-dimethyl-7-methyleneandrosta-1,4-diene-3,17-dione;
4-chloro-6-methyl-7-methylenandrosta-1,4-diene-3,17-dione;
4-fluoro-6-methyl-7-methylenandrosta-1,4-diene-3,17-dione;
16-fluoro-1,6-dimethyl-4-chloro-7-methylenandrosta-1,4-diene-3,17-dione and
4,16-difluoro-1,6-dimethyl-7-methylenandrosta-1,4-diene-3,17-dione either as single α- or β-epimer or as a mixture thereof.

8. A compound selected from the group consisting of:
7-methylenandrost-1,4-diene-3,17-dione;
1-methyl-7-methylenandrost-1,4-diene-3,17-dione;
4-chloro-7-methylenandrost-1,4-diene-3,17-dione;
4-fluoro-7-methylenandrost-1,4-diene-3,17-dione;
1-methyl-4-chloro-7-methylenandrost-1,4-diene-3,17-dione; and
1-methyl-4-fluoro-7-methylenandrost-1,4-diene-3,17-dione.

* * * * *

UNITED STATES PATENT AND TRADEMARK OFFICE
CERTIFICATE OF CORRECTION

PATENT NO. : 4,824,830
DATED : April 25, 1989
INVENTOR(S) : BUZZETTI et al

Page 1 of 3

It is certified that error appears in the above-identified patent and that said Letters Patent is hereby corrected as shown below:

On the cover page, Item [57], line 6 after the formula, "(x)" should read --(x)--;

line 8 after the formula, "(y)" should read --(y)--;

line 11 after the formula, "(x)" should read --(x)--;

line 13 after the formula, "(y)" should read --(y)--.

Column 1, lines 51 to 62, the formula should read:

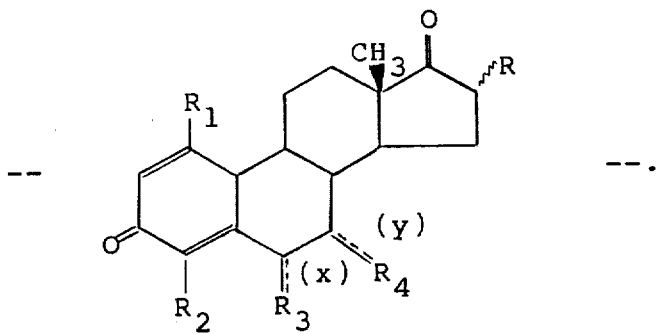

Column 2, line 5, "(x)" should read --(x)--;

line 10, "(y)" should read --(y)--;

line 15, "(x)" should read --(x)--;

line 20, "(y)" should read --(y)--.

UNITED STATES PATENT AND TRADEMARK OFFICE
CERTIFICATE OF CORRECTION

PATENT NO. : 4,824,830
DATED : April 25, 1989
INVENTOR(S) : BUZZETTI et al

It is certified that error appears in the above-identified patent and that said Letters Patent is hereby corrected as shown below:

Column 13, lines 52 to 62, the formula should read:

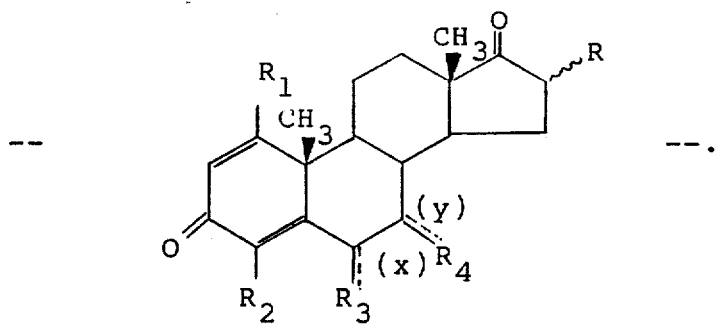

Column 14, line 5, "(x)" should read --(x)--;

line 10, "(y)" should read --(y)--;

line 15, "(x)" should read --(x)--;

line 20, "(y)" should read --(y)--;

lines 35 to 45, the formula should read:

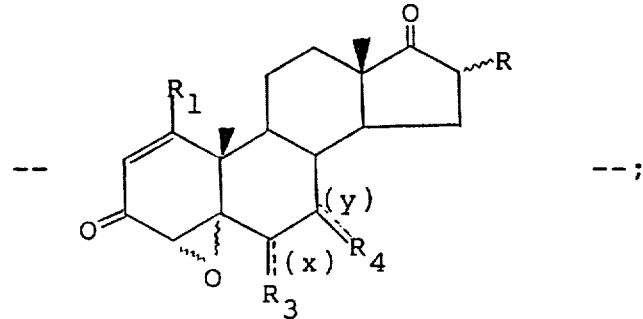

UNITED STATES PATENT AND TRADEMARK OFFICE
CERTIFICATE OF CORRECTION

PATENT NO. : 4,824,830
DATED : April 25, 1989
INVENTOR(S) : BUZZETTI et al

It is certified that error appears in the above-identified patent and that said Letters Patent is hereby corrected as shown below:

Column 14, line 49, "$\underline{(x)}$ and $\underline{(y)}$" should read --$\underline{\underline{(x)}}$ and $\underline{\underline{(y)}}$--.

Column 15, line 1, "$\underline{(x)}$ and $\underline{(y)}$" should read --$\underline{\underline{(x)}}$ and $\underline{\underline{(y)}}$--.

Signed and Sealed this

Sixteenth Day of October, 1990

Attest:

HARRY F. MANBECK, JR.

*Attesting Officer*     *Commissioner of Patents and Trademarks*